United States Patent
Bae et al.

(10) Patent No.: US 10,525,079 B2
(45) Date of Patent: Jan. 7, 2020

(54) PHARMACEUTICAL COMPOSITION FOR PREVENTING OR TREATING BREAST CANCER INCLUDING CRYSTALLINE POLYMORPH OF TETRAARSENIC HEXOXIDE, AND METHOD FOR PRODUCING SAME

(71) Applicant: CHEMAS CO., LTD., Seoul (KR)

(72) Inventors: Ill Ju Bae, Gangwon-do (KR); Zenglin Lian, Beijing (CN)

(73) Assignee: CHEMAS CO., LTD., Seoul (KR)

( * ) Notice: Subject to any disclaimer, the term of this patent is extended or adjusted under 35 U.S.C. 154(b) by 0 days.

(21) Appl. No.: 16/462,011

(22) PCT Filed: Nov. 17, 2017

(86) PCT No.: PCT/KR2017/013148
§ 371 (c)(1),
(2) Date: May 17, 2019

(87) PCT Pub. No.: WO2018/093215
PCT Pub. Date: May 24, 2018

(65) Prior Publication Data
US 2019/0328780 A1    Oct. 31, 2019

(30) Foreign Application Priority Data
Nov. 21, 2016   (KR) .................. 10-2016-0155228

(51) Int. Cl.
*A61K 33/36*   (2006.01)
*A61P 35/04*   (2006.01)

(52) U.S. Cl.
CPC .............. *A61K 33/36* (2013.01); *A61P 35/04* (2018.01)

(58) Field of Classification Search
CPC ................................. A61K 33/36; A61P 35/04
See application file for complete search history.

(56) References Cited

U.S. PATENT DOCUMENTS

| 2002/0028253 | A1 | 3/2002 | Bae et al. |
| 2011/0250292 | A1 | 10/2011 | Bae et al. |
| 2015/0017253 | A1 | 1/2015 | Kim |

FOREIGN PATENT DOCUMENTS

| KR | 10-0272835 B1 | 11/2000 |
| KR | 10-2004-0014813 A | 2/2004 |
| KR | 10-2010-0054210 A | 5/2010 |
| KR | 10-20100069204 A | 6/2010 |
| KR | 10-2013-0110466 A | 10/2013 |

OTHER PUBLICATIONS

International Search report issued for International Application No. PCT/KR2017/013148 dated Mar. 19, 2018, 4 pages.

*Primary Examiner* — Trevor Love
(74) *Attorney, Agent, or Firm* — Rothwell, Figg, Ernst & Manbeck, P.C.

(57) ABSTRACT

The present invention relates to a pharmaceutical composition for preventing or treating breast cancer which includes tetraarsenic hexoxide in which a crystalline polymorph a($As_4O_6$-a), of tetraarsenic hexoxide is 99% or higher, and to a method for producing the same. The composition of the present invention exhibits excellent effects of inhibiting the proliferation and metastasis of cancer cells, and thus can be usefully used as an anticancer agent.

5 Claims, 5 Drawing Sheets

PHARMACEUTICAL COMPOSITION FOR PREVENTING OR TREATING BREAST CANCER INCLUDING CRYSTALLINE POLYMORPH OF TETRAARSENIC HEXOXIDE, AND METHOD FOR PRODUCING SAME

CROSS-REFERENCE TO RELATED APPLICATIONS

The application is a 35 U.S.C. § 371 National Phase Entry Application from PCT/KR2017/013148, filed on Nov. 17, 2017, which claims the benefit of Korean Patent Application No. 10-2016-0155228 filed on Nov. 21, 2016, the disclosures of which are incorporated herein in their entirety by reference.

TECHNICAL FIELD

The present invention relates to a pharmaceutical composition containing a crystalline polymorph of tetraarsenic hexoxide for prevention or treatment of breast cancer.

BACKGROUND ART

Cancer is characterized by uncontrolled cell growth, and such abnormal cell growth forms a mass of cells called a tumor, which penetrates into surrounding tissues, and, in severe cases, causes metastasis into other organs of the body. Academically, tumors are called neoplasia. Cancer affects all tissues and organs of the body at various prevalence rates.

Since the incidence of breast cancer is gradually increasing due to the improvement of living standards owing to economical growth, changes and westernization of eating habits, changes of childbirth and breastfeeding methods, and the like, breast cancer takes first place among female tumors (Kamangar F., et al., 2006). Breast cancer is a malignant tumor that can spread to other organs to threaten ones' life, unlike benign tumors staying in the breast. The beast cancer including metastatic breast cancer to solid tumors has a wide variety of biological characteristics, and thus has various therapeutic options and prognoses.

Although recent developments of radical excision, chemotherapy, and hormone therapy have significantly improved the treatment results of breast cancer, breast cancer recurs in approximately 25-30% of patients without axillary lymph node metastasis and approximately 75-80% of patients with axillary lymph node metastasis within 10 years, and most of these patients die from metastatic breast cancer. As the number of breast cancer patients steadily increases, patients with metastatic breast cancer are also increasing, and therefore, research continues on early breast cancer patients as well as treatment methods of these patients, prognosis, and factors affecting the prognosis, but the results are yet insignificant.

Therefore, with respect to breast cancer treatment, there is a continuing need for the development of therapeutic agents having excellent anti-cancer effects regardless of the presence or absence of breast cancer metastasis.

The present inventors have already received patent rights of technical features wherein tetraarsenic hexoxide purified from natural arsenolite containing arsenic through separation and purification techniques showed cancer metastasis suppressing effects in animal experiments and had excellent anticancer treatment effects when administered to end-stage cancer patients with uterine cancer, bladder cancer, lung cancer, maxillary sinus cancer, kidney cancer, and the like (Korean Patent No. 272835).

The present inventors, as a result of continuous research on arsenic, revealed that tetraarsenic hexoxide having 99% or more of tetraarsenic hexoxide crystalline polymorph a can be produced by a novel preparation method, different from the method disclosed in the above registered patent, and a composition containing such tetraarsenic hexoxide has a remarkable effect on breast cancer prevention or treatment, and completed the present invention.

DETAILED DESCRIPTION OF THE INVENTION

Technical Problem

An aspect of the present invention is to provide a pharmaceutical composition containing a crystalline polymorph of tetraarsenic hexoxide ($As_4O_6$) as an active ingredient for prevention or treatment of breast cancer.

Another aspect of the present invention is to provide a method for preparing a pharmaceutical composition containing a crystalline polymorph of tetraarsenic hexoxide ($As_4O_6$) as an active ingredient for prevention or treatment of breast cancer.

Another aspect of the present invention is to provide a pharmaceutical composition containing a crystalline polymorph of tetraarsenic hexoxide ($As_4O_6$) as an active ingredient for inhibition of breast cancer metastasis.

Technical Solution

The present invention is directed to a pharmaceutical composition containing tetraarsenic hexoxide as an active ingredient for prevention or treatment of breast cancer, wherein the tetraarsenic hexoxide includes 99% or more of tetraarsenic hexoxide crystalline polymorph a ($As_4O_6$-a).

The tetraarsenic hexoxide of the composition may be prepared by: a first step of heating sodium chloride at 100~800° C., followed by cooling; a second step of placing arsenic trioxide ($As_2O_3$) on the sodium chloride, followed by heating from 100° C. to 1000° C. in an airtight state and then cooling; a third step of separating crystals crystallized in a filter bed collecting sublimated arsenic; and a fourth step of repeating the second and third steps four to ten times using the crystals obtained in the third step instead of the arsenic trioxide in the second step, thereby obtaining tetraarsenic hexoxide crystals.

The tetraarsenic hexoxide of the composition may include less than 1% of tetraarsenic hexoxide crystalline polymorph b ($As_4O_6$-b).

The tetraarsenic hexoxide may have a purity of 99.9% or more.

The $As_4O_6$-a and $As_4O_6$-b may have features (i) to (iii) below.

TABLE 1

| Category | Crystalline polymorph a ($As_4O_6$-a) | Crystalline polymorph b ($As_4O_6$-b) |
|---|---|---|
| (i) Cell parameters | a = b = c = 11.0734 Å<br>$\alpha = \beta = \gamma = 90°$<br>V = 1357.82 Å$^3$ | a = b = c = 11.0600 Å<br>$\alpha = \beta = \gamma = 90°$<br>V = 1352.90 Å$^3$ |

TABLE 1-continued

| Category | Crystalline polymorph a ($As_4O_6$-a) | Crystalline polymorph b ($As_4O_6$-b) |
|---|---|---|
| (ii) As—O bond length | 1.786 Å | 2.011 Å |
| (iii) O—As—O bond angle | 98.36° | 109.47° |

Figure 1:
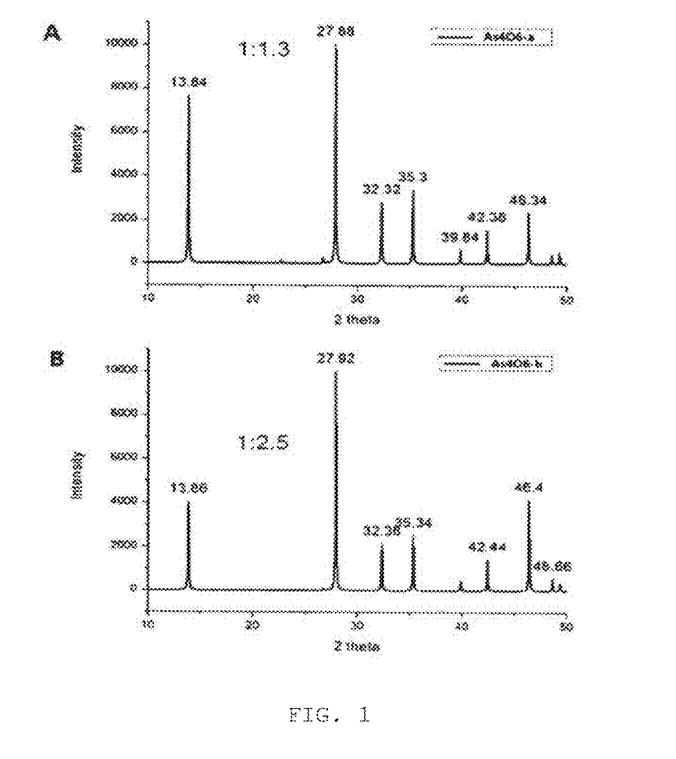
FIG. 1 shows X-ray powder diffraction spectrogram of $As_4O_6$-a and $As_4O_6$-b.

The $As_4O_6$-a has a crystal form, of which the X-ray powder diffraction spectrum obtained by using a light source wavelength of 1.5406 Å within a diffraction angle (2θ) of 10° to 50° at a rate of 1°/min (scan step of 0.02°) shows peaks at 2θ values of 13.84, 27.88, 32.32, 35.3, 39.84, 42.38, 46.34, 48.6, and 49.34 (see FIG. 1). In addition, the ratio of main peaks shown at 2θ values of 13.8 and 27.9 is 1:1.3.

The $As_4O_6$-b has a crystal form, of which the X-ray powder diffraction spectrum obtained by using a light source wavelength of 1.5406 Å within a diffraction angle (2θ) of 10° to 500 at a rate of 1/min (scan step of 0.020) shows peaks at 2θ values of 13.86, 27.92, 32.36, 35.34, 39.9, 42.44, 46.4, 48.66, and 49.4 (see FIG. 1). In addition, the ratio of main peaks shown at 2θ values of 13.8 and 27.9 is 1:2.5.

In accordance with another aspect of the present invention, there is provided a pharmaceutical composition containing tetraarsenic hexoxide as an active ingredient for inhibiting breast cancer metastasis, wherein the tetraarsenic hexoxide includes 99% or more of tetraarsenic hexoxide crystalline polymorph a ($As_4O_6$-a).

Hereinafter, the present invention will be described in detail.

The present invention is directed to a pharmaceutical composition containing tetraarsenic hexoxide ($As_4O_6$) as an active ingredient for prevention or treatment of breast cancer, wherein the tetraarsenic hexoxide includes 99% or more of tetraarsenic hexoxide crystalline polymorph a ($As_4O_6$-a).

In accordance with another aspect of the present invention, there is provided a method for preparing a pharmaceutical composition containing a crystalline polymorph of tetraarsenic hexoxide ($As_4O_6$) as an active ingredient for prevention or treatment of breast cancer, the method including: a first step of heating sodium chloride at 100~800° C., followed by cooling; a second step of placing arsenic trioxide ($As_2O_3$) on the sodium chloride, followed by heating from 100° C. to 1000° C. in an airtight state and then cooling; a third step of separating crystals crystallized in a filter bed collecting sublimated arsenic; and a fourth step of repeating the second and third steps four to ten times using the crystals obtained in the third step instead of the arsenic trioxide in the second step, thereby obtaining tetraarsenic hexoxide crystals, wherein the tetraarsenic hexoxide crystals obtained in the fourth step include 99% or more of tetraarsenic hexoxide crystalline polymorph a ($As_4O_6$-a).

A synthesis reactor of a kaolin material and clamps capable of mounting filters thereon above the synthesis reactor are prepared. Then, sodium chloride is placed in the synthesis reactor, and heated and cooled. The reason why sodium chloride is used in the preparation method of the present invention is that when heating is carried out while arsenic trioxide is placed on the sodium chloride in the second step, heat is uniformly transferred to arsenic compounds, thereby helping the sublimation of the arsenic compounds. In order to remove impurities and moisture from such sodium chloride, the sodium chloride is heated at 100-800° C. for 2-6 hours in the first step. In the first step, the sodium chloride is cooled at room temperature for 3-10 hours after the heating.

Then, the second step is conducted by placing arsenic trioxide ($As_2O_3$) on the sodium chloride, followed by heating from 1001 to 1000 in an airtight state and then cooling. Here, after the placing of arsenic trioxide, three to six filters (filter beds) capable of collecting sublimated arsenic are mounted on the clamps such that the intervals between the filters are 2-6 mm. The filters used herein preferably have a basic weight of 70-100 g/m², a thickness of 0.17-0.25 mm, a filtration speed of 22-30 s/100 ml, and a retention rate of 5-10 μm.

After the mounting of the filters, an airtight state was made, and then a bottom portion of the synthesis reactor is heated for 3-10 hours while the temperature is gradationally raised from 100° C. to 1000° C., so that the temperature of the center portion of the highest filter bed is maintained at 150±100° C., and tetraarsenic hexoxide is crystallized passing through the filter beds. Then, cooling is carried out at room temperature for 5 hours or longer, and preferably 5-10 hours.

Then, the third step is conducted by separating white crystals collected in the three to six spaced filter beds installed in a stacked type.

After a small amount of arsenic trioxide remaining on the sodium chloride in the synthesis reactor is removed, the collected white crystals are placed thereon, and then the second and third steps are repeated four to ten times in the same conditions, thereby finally obtaining tetraarsenic hexoxide crystals. As a result of checking the crystal structures obtained according to the preparation method of the present invention, it was verified that most of the crystals were $As_4O_6$-a, which accounted for 99% or more.

The pharmaceutical composition containing a crystalline polymorph of tetraarsenic hexoxide of the present invention can be favorably used in the prevention or treatment of breast cancer and the inhibition of breast cancer metastasis.

The pharmaceutical composition of the present invention may be formulated in the form of: an oral formulation, such as a powder, granules, a tablet, a capsule, a suspension, an emulsion, a syrup, or an aerosol; an externally applied preparation; a suppository; and a sterile injectable solution, according to usual methods, respectively. Examples of a carrier, an excipient, and a diluent that may be contained in the pharmaceutical composition may include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate, and mineral oil. The pharmaceutical composition may be formulated into preparations by using a diluent or an excipient, such as a filler, an extender, a binder, a wetting agent, a disintegrant, or a surfactant. A solid preparation for oral administration includes a tablet, a pill, a powder, granules, a capsule, and the like. These solid preparations may be prepared by mixing the tetraarsenic hexoxide of the present invention with at least one excipient, for example, starch, calcium carbonate, sucrose or lactose, gelatin, or the like. Also, lubricants, such as magnesium stearate and talc, may be used in addition to simple excipients. A liquid preparation for oral administration corresponds to a suspension, a liquid for internal use, an emulsion, a syrup, and the like, and may include simple diluents that are frequently used, such as water and liquid paraffin, and several excipients, such as a wetting agent, a sweetener, an aromatic agent, and a preservative. A preparation for parenteral administration includes a sterile aqueous solution, a non-aqueous solvent, a suspension, an emulsion, a freeze-drying agent, and a suppository. The non-aqueous solvent and the suspension may include propylene glycol, polyethylene glycol, vegetable oils such as olive oil, injectable esters such as ethylolate, and the like. A base material for the suppository may include Witepsol, Macrogol, Tween 61, cacao butter, laurin butter, glycerogelatin, and the like.

The dose of the pharmaceutical composition may vary depending on age, gender, and body weight of a subject to be treated, a particular disease or pathological condition to be treated, severity of a disease or pathological condition, route of administration, and determination of a prescriber. The determination of the dose based on these factors is within the level of a person skilled in the art, and the general dose is in the range of approximately 0.01-500 mg/kg/day. A more preferable dose is 0.1-100 mg/kg/day. The administration may be carried out once a day or several times in a divided dose a day. The above dose is not intended to restrict the scope of the present invention in any way.

The pharmaceutical composition may be administered to mammals, such as rats, domestic animals, and humans, via various routes. All manners of administration may be predicted, and for example, the administration may be carried out through oral, rectal, intravenous, intramuscular, subcutaneous, endometrial, intracerebroventricular injection.

Advantageous Effects

The pharmaceutical compositions for prevention or treatment of breast cancer of the present invention have excellent anticancer effects by containing tetraarsenic hexoxide including 99% or more of tetraarsenic hexoxide crystalline polymorph a.

Furthermore, the pharmaceutical compositions of the present invention were verified to have an excellent effect of inhibiting breast cancer metastasis.

MODE FOR CARRYING OUT THE INVENTION

Hereinafter, preferable examples of the present invention will be described in detail. However, the present invention is not limited to the examples described herein, and thus may be embodied into different forms. Rather, these examples are provided so that this disclosure will be thorough and complete, and will fully convey the scope of the invention to those skilled in the art.

Example 1: Preparation of Present Tetraarsenic Hexoxide

A synthesis reactor (100 mm in height and 190 mm in diameter) specially manufactured using kaolin and three to six clamps capable of mounting filters thereon were prepared. A first clamp was installed at a distance of 50 mm from the synthesis reactor, and second to sixth clamps were installed above the first clamp at intervals of 2-6 mm from the first stamp, and the dimension of each clamp was 210 mm in diameter and 10 mm in thickness.

Coarse salt weighing 400-600 g (a moisture content of 10% or less) was introduced into the synthesis reactor, and then evenly spread out and packed to a thickness of about 20 mm. The synthesis reactor was slowly heated at 100-800° C. for 3 hours, and continuously heated such that the surface temperature of the salt was 290±30° C. inside the reactor, thereby removing moisture and impurities. Then, cooling was carried out at room temperature for 5 hours.

Then, 100 g of a raw material, $As_2O_3$ (a purity of 98% or higher, prepared by YUNNAN WENSHAN JINCHI ARSENIC CO., LTD.) was placed on the coarse salt inside the synthesis reactor, and filters (filter beds) capable of collecting sublimated arsenic were mounted on the three to six clamps installed above the synthesis reactor such that the intervals between the filters were 2-6 mm. The filters used herein preferably had a basic weight of 70-100 g/m$^2$, a thickness of 0.17-0.25 mm, a filtration speed of 22-30 s/100 ml, and a retention rate of 5-10 μm.

The filters were fixed using the clamps, and then heat was applied to the bottom portion of the synthesis reactor to gradationally raise the temperature from 100° C. to 1,000° C. First, the bottom portion of the synthesis reactor was heated for 1 hour so that the temperature outside the bottom portion of the synthesis reactor was about 350±1000° C., and thereafter, heating was carried out such that the temperature outside the bottom portion of the synthesis reactor was about 600-650° C. and about 700-1,000° C., so the temperature of the center portion of the highest filter bed was maintained at 150±100° C. through heating for a total of 5-10 hours. Then, cooling was carried out at room temperature for 5-7 hours. In this procedure, the $As_2O_3$ powder placed on the salt inside the synthesis reactor transformed into a gas inside the synthesis reactor, and the gas moved up, and then transformed into a liquid since the upper temperature outside the synthesis reactor was relatively low, and thereafter, the liquid was crystallized as a solid, and thus white crystals were generated on the filters.

The collected white crystals were placed on the coarse salt inside the synthesis reactor, and the heating, cooling, and crystal collecting processes were again repeated four times, thereby finally obtaining 12.0 g of the crystals. As a result of checking the structure of the obtained arsenic compound crystals, it was confirmed that most of the crystals were $As_4O_6$-a while 99 wt % or more of $As_4O_6$-a and less than 1 wt % of $As_4O_6$-b were obtained.

It was confirmed that as for the differential scanning calorimetry (DSC) value at a temperature rise rate of 10 V/min, $As_4O_6$-a showed an endothermic peak (melting point) at 282.67 and $As_4O_6$-b showed an endothermic peak (melting point) at 286.77° C.

X-ray powder diffraction spectra of $As_4O_6$-a and $As_4O_6$-b are shown in FIG. 1, and diffraction data of $As_4O_6$-a and $As_4O_6$-b are shown in Table 2 below.

TABLE 2

| $As_4O_6$-a | | $As_4O_6$-b | |
|---|---|---|---|
| 2θ (°) | Diffraction intensity | 2θ (°) | Diffraction intensity |
| 13.84 | 7631.01 | 13.86 | 4012.09 |
| 27.88 | 10000 | 27.92 | 10000 |
| 32.32 | 2801.74 | 32.36 | 2130.23 |
| 35.3 | 3369.82 | 35.34 | 2511 |
| 39.84 | 623.242 | 39.9 | 447.422 |
| 42.38 | 1551.5 | 42.44 | 1431.86 |
| 46.34 | 2345.2 | 46.4 | 4159.8 |
| 48.6 | 447.69 | 48.66 | 564.995 |
| 49.34 | 502.761 | 49.4 | 375.571 |

As confirmed in FIG. 1 and Table 2, the ratio of main peaks shown at 2θ values of 13.8 and 27.9 was 1:1.3 in $As_4O_6$-a, and the ratio of main peaks shown at 2θ values of 13.8 and 27.9 was 1:2.5 in $As_4O_6$-b. DSC analysis, structure determination, and X-ray diffraction analysis of the prepared compounds were carried out by the following methods.

(1) DSC Analysis

Using a DSC system (SDT Q600 V20.9 Build 20), 20.0 mg of a sample was analyzed while the temperature was raised to 310° C. at a temperature rise rate of 10'/min with $N_2$ flowing out at 100 mL/min.

(2) X-Ray Crystallography

Single crystals of tetraarsenic hexoxide ($As_4O_6$, MW=395.6) were placed on a glass fiber and then an X-ray beam was applied thereto, to observe diffraction patterns on photographic films and the presence or absence of the organization of diffraction data, thereby determining space groups and cell parameters. Diffraction intensities were collected in the range of 10°<2θ<50°. The crystal structure of $As_4O_6$ was determined from the data by the Patterson method by using a structure determination program (SHELXTL program).

(3) X-Ray Diffractometry

A sample was prepared by pulverizing the obtained crystals into particles having a size of 10-30 μm (−325 mesh), filling a glass holder for X-ray diffraction analysis (20 mm×16 mm×1 mm) with the particles, compressing the particles by a glass slide or the like, and flattening the particles to allow a sample surface to be parallel with a holder surface. The X-ray diffraction spectrum of the crystals was drawn using Cu Kai (1.54060 Å) of XRD within a diffraction angle (2θ) of 10° to 50° at a rate of 1°/min (scan step of 0.02°).

Comparative Example 1: Preparation of Tetraarsenic Hexoxide

A synthesis reactor (100 mm in height and 190 mm in diameter) specially manufactured using kaolin and three to six clamps capable of mounting filters thereon were prepared. A first clamp was installed at a distance of 50 mm from the synthesis reactor, and second to sixth clamps were installed above the first clamp at intervals of 2-6 mm from the first stamp, and the dimension of each clamp was 210 mm in diameter and 10 mm in thickness.

Coarse salt weighing 400-600 g (a moisture content of 10- or less) was introduced into the synthesis reactor, and then evenly spread out and packed to a thickness of about 20 mm. The synthesis reactor was slowly heated at 100-800° C. for 3 hours, and continuously heated such that the surface temperature of the salt was 290±30° inside the reactor, thereby removing moisture and impurities. Then, cooling was carried out at room temperature for 5 hours.

Then, 100 g of a raw material, $As_2O_3$ (a purity of 98% or higher, prepared by YUNNAN WENSHAN JINCHI ARSENIC CO., LTD.) was placed on the coarse salt inside the synthesis reactor, and filters (filter beds) capable of collecting sublimated arsenic were mounted on the three to six clamps installed above the synthesis reactor such that the intervals between the filters were 2-6 mm. The filters used herein preferably had a basic weight of 70-100 g/m², a thickness of 0.17-0.25 mm, a filtration speed of 22-30 s/100 ml, and a retention rate of 5-10 μm.

The filters were fixed using the clamps, and then heat was applied to the bottom portion of the synthesis reactor to gradationally raise the temperature from 100° C. to 1,000° C. First, the bottom portion of the synthesis reactor was heated for 1 hour such that the temperature outside the bottom portion of the synthesis reactor was about 350±100° C., and thereafter, heating was carried out such that the temperature outside the bottom portion of the synthesis reactor was about 600-650° C. and about 700-1,000° C., so the temperature of the center portion of the highest filter bed was maintained at 150±100° C. through heating for a total of 5-10 hours. Then, cooling was carried out at room temperature for 5-7 hours. In this procedure, the $As_2O_3$ powder placed on the salt inside the synthesis reactor transformed into a gas inside the synthesis reactor, and the gas moved up, and then transformed into a liquid since the upper temperature outside the synthesis reactor was relatively low, and thereafter, the liquid was crystallized as a solid, and thus white crystals were generated on the filters. 48.5 g of crystals were collected from the filters. As a result of checking the crystal structure of the collected arsenic compounds, it was confirmed that $As_4O_6$-b accounted for 99% or more.

Comparative Examples 2 to 4: Preparation of Tetraarsenic Hexoxide

Comparative Examples 2 and 3 were prepared by mixing Example 1 (composition having 99% or more of crystalline polymorph $As_4O_6$-a) and Comparative Example 1 (composition having 99% or more of crystalline polymorph $As_4O_6$-b) at 4:1 and 1:1, respectively.

Test Example 1: Test of Human Breast Cancer Cell Proliferation Inhibitory Effects (1) Materials and Cell Culture Fetal bovine serum (FBS) and cell culture medium were prepared (Hyclone), and dimethyl sulfoxide (DMSO) and 3-(4,5-dimetyl-thiazol-2yl)-2,5-diphenyltetrazolium bromide (MTT, Amresco LLC, USC) were prepared.

As human cancer cell lines, human breast cancer cells MCF-7 and SK-BR-3 were obtained from the Shanghai Cell Bank of Chinese Academy of Sciences. The MCF-7 cells were incubated in Minimum Essential Media (MEM) supplemented with 10% FBS, 100 U/ml penicillin, and 100 μg/ml streptomycin and the SK-BR-3 cells were incubated in Dulbecco's modified Eagle's medium (DMEM) supplemented with 10% FBS, 100 U/ml penicillin, and 100 µg/ml streptomycin in a humidified incubator with 5% $CO_2$ and 95% air. The media were exchanged every three days.

(2) Cell Proliferation Assay (MTT Assay)

The effects of Example 1 and Comparative Examples 1 to 3 on cell proliferation were assessed using MTT assay. MTT assay is based on the ability of viable cells against MTT to produce insoluble dark blue formazan products. After the cells were suspended in the medium by trypsin treatment and collected, the cells were dispensed at a density of $4\times10^3$ cells/well in a 96-well culture dish (Costar, Cambridge, Mass., USA). After 24 hours, the cells in the media containing 10% FBS were treated with Example 1 and Comparative Examples 1 to 3, at 0, 0.625, 1.25, 2.5, 5, 10, 20, 40, or 80 µM, and then incubated. Here, stock solutions obtained by dissolving Example 1 and Comparative Examples 1 to 3 at $5\times10^{-2}$ M in 1 M sodium hydroxide was used. For MTT assay for cell proliferation, supernatants were removed from the cells incubated for 48 hours, and 72 hours after the sample treatment, and 20 µl of 5 mg/me MTT solution was added per well, and the cells were incubated at 37° C. for 4 hours to form formazan crystals. After the incubation, supernatants were again removed, followed by addition of 100 µl of DMSO to every well, and then mixing was carried out to completely dissolve dark blue crystals. All the crystals were completely dissolved by standing at room temperature for 15 minutes, and the absorbance was measured using a microplate reader at a wavelength of 570 nm ($A_{570\ nm}$).

(3) Statistical Analysis

The absorbance value of the control group treated without the sample was calculated as 100, and the absorbance value of the treatment group treated with the sample, compared with that of the control group, was calibrated, and the percentage of inhibition of cell proliferation was calculated according to the following equation.

Percentage (%) of inhibition of cell proliferation=
((mean absorbance of control group cells−mean absorbance of treatment group cells)/mean absorbance of control group cells)×100

All data were expressed as mean±standard error of the mean (mean±SEM). One-way analysis of variance (ANOVA) followed by Dunnett's post-test was used to perform multiple comparison. Statistical significance was defined as $p<0.05$, and each test was repeated three times.

(4) Results of Test Using MCF-7 Cells

Figure 2:
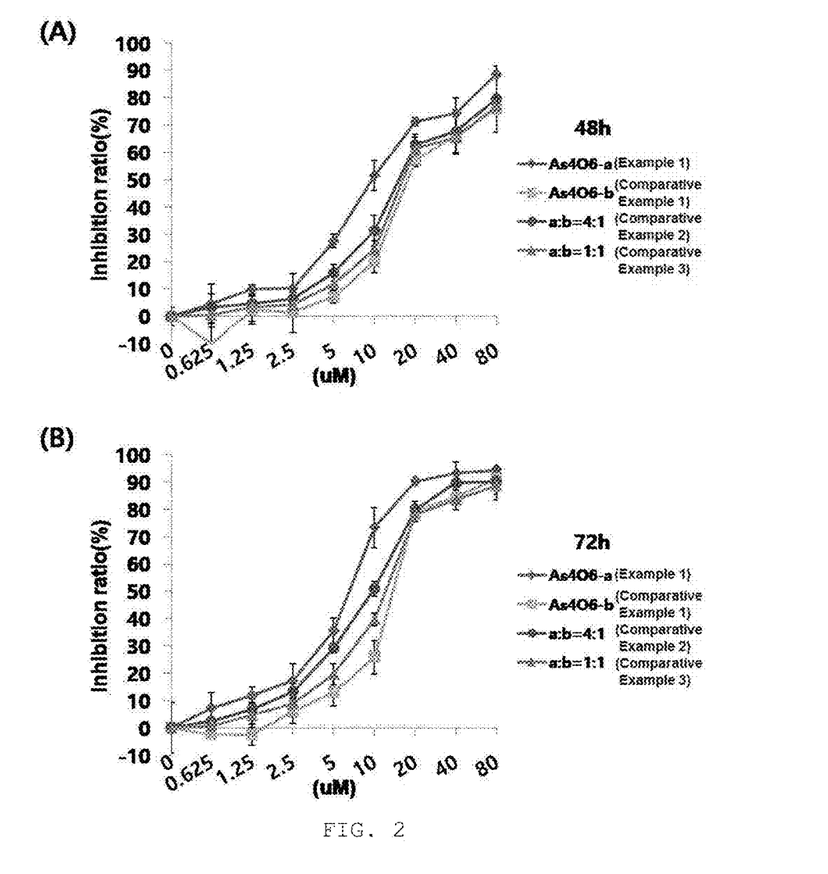
FIG. 2 shows graphs depicting the results of assessing cell proliferation inhibitory effects through MTT assay after MCF-7 cells were treated with Example 1 and Comparative Examples 1 to 3 and incubated for 48 hours (FIG. 2A) and 72 hours (FIG. 2B).

The human breast cancer cell line MCF-7 cells were treated with Example 1 and Comparative Examples 1 to 3, and incubated for 48 and 72 hours, followed by MTT assay. The results are shown in FIG. 2. It was confirmed that the percentages of inhibition of the breast cancer cell line MCF-7 cell proliferation were higher in the treatment with Example 1 and then the incubation for 48 hours (FIG. 2A) and 72 hours (FIG. 2B) compared with the treatment with Comparative Example 1. It was also confirmed that the percentage of inhibition of MCF-7 cell proliferation was higher in Example 1 than Comparative Example 2 or 3 in which Example 1 and Comparative Example 1 were mixed at 4:1 or 1:1.

(5) Results of Test Using SK-BR-3 Cells

Figure 3:
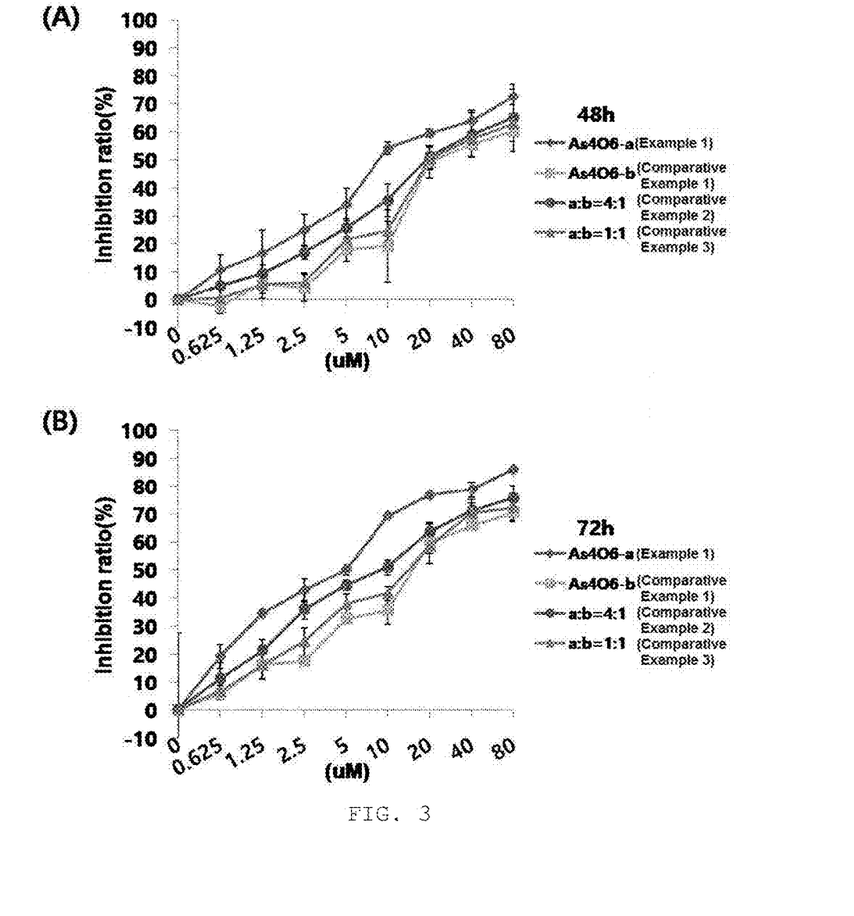
FIG. 3 shows graphs depicting the results of assessing cell proliferation inhibitory effects through MTT assay after SK-BR-3 cells were treated with Example 1 and Comparative Examples 1 to 3 and incubated for 48 hours (FIG. 3A) and 72 hours (FIG. 3B).

The human breast cancer cell line SK-BR-3 cells were treated with Example 1 and Comparative Examples 1 to 3, and incubated for 48 and 72 hours, followed by MTT assay. The results are shown in FIG. 3. It was confirmed that the percentages of inhibition of the breast cancer cell line SK-BR-3 cell proliferation were higher in the treatment with Example 1 and then the incubation for 48 hours (FIG. 3A) and 72 hours (FIG. 3B) compared with the treatment with Comparative Example 1. It was also confirmed that the percentage of inhibition of SK-BR-3 cell proliferation was higher in Example 1 than Comparative Example 2 or 3 in which Example 1 and Comparative Example 1 were mixed at 4:1 or 1:1.

Test Example 2: Test on Effect of Inducing Human Breast Cancer Cell Apoptosis (1) Materials and Cell Culture Fetal bovine serum (FBS) and cell culture medium were prepared (Hyclone). RT-PCR Kit and Trizol were obtained from Takara Biotechnology CO., LTD., and Annexin V-FITC was obtained from Shanghai Biyuntian Biological Technology Co., LTD. Primers were designed and synthesized by Beijing Aodingkangsheng Biological Technology Co., LTD.

Human breast cancer cells MCF-7, as a human cancer cell line, were obtained from the Shanghai Cell Bank of Chinese Academy of Sciences. MCF-7 cells were incubated in Minimum Essential media (MEM) supplemented with 10% FBS, 100 U/ml penicillin, and 100 µg/m streptomycin in a humidified incubator with 5% $CO_2$ and 95% air. The media were exchanged every three days.

(2) Flow Cytometry

Figure 4:
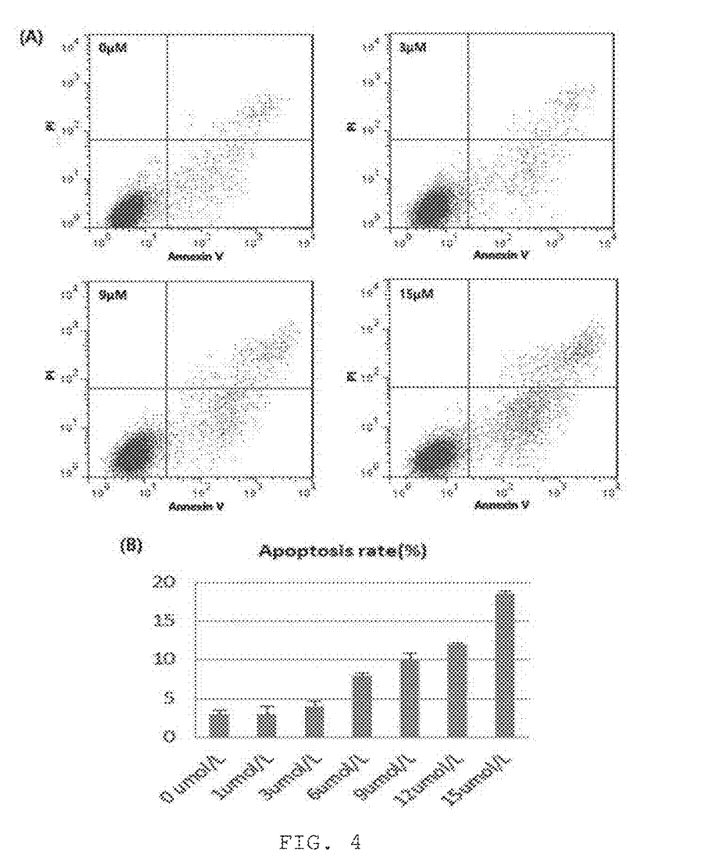
FIG. 4 shows the results of detecting annexin V and PI, which label cells, through flow cytometry (4A), with respect to the cell apoptotic effect according to concentration of Example 1 when MCF-7 cells were treated with Example 1 of different concentrations, and the results of investigating cell apoptosis rate by analyzing the amount of annexin V compared with PI (4B).

The effect of Example 1 on the induction of cell apoptosis was assessed by flow cytometry. The cells were dispensed at $1\times10^5$ cells/well in a 6-well culture dish, and incubated for 24 hours. After 24 hours, the cells contained in the MEM containing 10% FBS were treated with Example 1 at 0, 1, 3, 6, 9, 12 or 15 µM, and incubated for 24 hours. After 24 hours, the cells were treated using Annexin V-FITC kit to check cell apoptosis, and also treated with propidium iodide (PI) for distinguishment from natural cell death. Here, experiments were conducted according to the use methods of PI and Annexin V-FITC kit. The cells treated with the Annexin V-FITC kit were analyzed for the degree of cell apoptosis by using the BD FACS calibur flow cytometry system. The results are shown in FIG. 4. As a result of analysis through flow cytometry (4A) on the cells treated with Example 1 and then labeled with annexin V and PI and as a result of investigating cell apoptosis rates (4B) by analyzing the amount of annexin V compared with PI, it was confirmed that cell apoptosis increased with the increase in treatment concentration of Example 1.

(3) Reverse Transcription Polymerase Reaction (RT-PCR)

Figure 5:
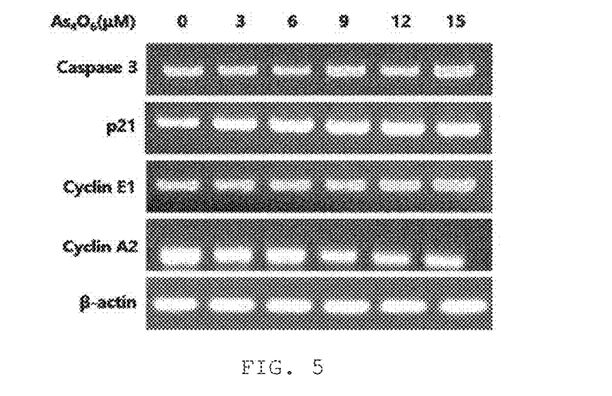
FIG. 5 shows the results of investigating the expression changes of genes, involved in cell cycle and cell apoptosis, according to the concentration of Example 1 when MCF-7 cells were treated with Example 1 of different concentrations.

In order to investigate the effect of Example 1 on the induction of cell apoptosis, mRNA expression levels of caspase-3, p21, cyclin E1, and cyclin A2, which are genes involved in cell cycle and apoptosis, were examined by RT-PCR. The cells were dispensed at $1\times10^5$ cells/well in a 6-well culture dish, and incubated for 24 hours. After 24 hours, the cells contained in the MEM containing 10% FBS were treated with Example 1 at 0, 1, 3, 6, 9, 12 or 15 µM, and incubated for 24 hours. After 24 hours, the cells were collected, and then RNA was extracted using Trizol reagent. The gene amplification was carried out using the primers on Table 3 below and the RT-PCR kit while the extracted RNA was used as a template, and then the changes in mRNA expression levels of caspase 3, p21, cyclin E1, and cyclin A2 were examined by electrophoresis on agarose gel. The results are shown in FIG. 5. Here, the expression level of 3-actin was also examined as a loading control group. As a result of the treatment with Example 1, the mRNA expressions of p21 and cyclin E1, which are genes regulating cell cycles relevant to cell apoptosis, and caspase-3, which is a gene involved in cell apoptosis, were increased with the increase in concentration of Example 1, while the mRNA expression of cyclin A2, which is a cell cycle regulation factor involved in cell proliferation, was decreased.

Therefore, it can be seen that the tetraarsenic hexoxide of Example 1 can treat breast cancer by inducing apoptosis of breast cancer cells.

TABLE 3

| Gene | Primer sequences (5' → 3') | Amplification length (bp) |
|---|---|---|
| β-actin | Up stream: TGACGTGGACATCCGaAAAG<br>Down stream: CTGGAAGGTGGACAGCGAGG | 206 |
| p21 | Up stream: ACATCTTCTGCCTTAGTCTCA<br>Down stream: GCCCCTTCAAAGTGCCATC | 426 |
| Caspase-3 | Up stream: TGGCAACAGAATTTGAGTCCT<br>Down stream: GCAGTTAAGTCATCCGTGTAT | 596 |
| Cyclin E1 | Up stream: GCCTTGTATCATTTCTCGTCAT<br>Down stream: CTCTGCTTCTTACCGCTCT | 305 |
| Cyclin A2 | Up stream: GTAAACAGCCTGCGTTCACC<br>Down stream: ACTTGAACTAACCAGTCCACGAG | 382 |

Test Example 3: Test to Investigate Breast Cancer Metastasis Inhibitory Effect

5-Week-old babl/c-nu male nude mice, which were safe from specific pathogens and respiratory diseases and had a body weight of 18-20 g, were used as experimental animals. The nude mice were allowed free access to food and water, and were bred in a 12-hr light/12-hr dark cycle for 7 days.

The mice were transplanted with human breast cancer cells, MDA-MB-231, through subcutaneous injection, and bred for 7 days. After 7 days, the mice were randomly divided, and then respective mice were orally administered with the compositions of Example 1 and Comparative Example 1 at 4.5 mg/kg for 7 days. Here, the mice treated with nothing after the transplantation of breast cancer cells were used as a control group. After 7 days of administration of the compositions, lung tissues were taken from the mice, and then cancer cells spread to the lungs were counted to compare the degree of inhibition of breast cancer metastasis.

As a result, it was confirmed that most of the transplanted breast cancer cells spread to the lungs in the control group treated with nothing after the transplantation of breast cancer cells, whereas the spreading of the breast cancer cells to the lungs was inhibited in the groups treated with Comparative Example 1 and Example 1. It was especially confirmed that Example 1 showed a percentage of inhibition of cancer cell metastasis of 90% or more, indicating a significantly excellent cancer metastasis inhibitory effect compared with Comparative Example 1 showing a percentage of inhibition of cancer cell metastasis of 50%.

Test Example 4: Clinical Test

The following clinical test was conducted using the composition of Example 1.

The patient received hospital treatments and folk remedies since breast cancer was found in 2006, but the breast cancer was metastasized to the lungs, pleura, bones, and liver. In May 2014, pleural effusion and peritoneal fluid collection were found, and thus the pleural effusion was extracted several times. However, due to a severe difficulty in breathing caused by malignant pleural effusion, the patient breathed through an oxygen respiratory system in an emergency room and hospice medical ward. However, the patient began to develop pallor due to a lack of oxygen, and the patient, having about one week left to live, was orally administered with 5 mg of Example 1 three times a day (15 mg/day).

Figure 6:
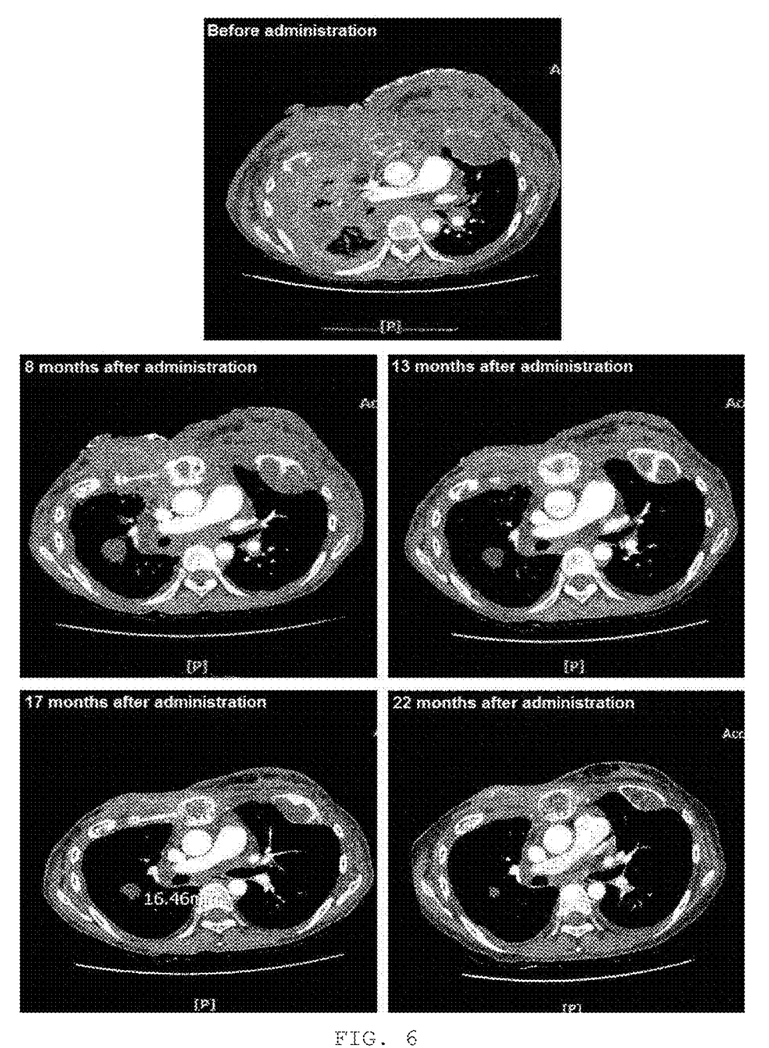
FIG. 6 shows CT images of the lungs before and after administration of Example 1 to a patient with metastatic breast cancer in clinical trials, confirming that the size of metastasized tumors decreased due to the administration of Example 1.

CT images of the patient before the administration of Example 1 and after 8, 13, 17 and 22 months of administration of Example 1 are shown in FIG. 6. Before the administration of Example 1, the airway was closed due to metastasis to the right lung and left lung, but after 8, 13, 17, and 22 months of administration, the sizes of the cancers in both of the lungs were decreased as the duration of administration increased.

It was confirmed through the clinical test results that the composition of the present invention had a metastatic breast cancer treatment effect.

The invention claimed is:

1. A pharmaceutical composition containing tetraarsenic hexoxide ($As_4O_6$) as an active ingredient for treatment of breast cancer, wherein the tetraarsenic hexoxide includes 99 wt % or more of tetraarsenic hexoxide crystalline polymorph a having features (i) to (iii) below:
   (i) Cell parameters:
   $a=b=c=11.0734$ Å
   $\alpha=\beta=\gamma=90°$
   $V=1357.82$ Å$^3$
   (ii) As—O bond length: 1.786 Å
   (iii) O—As—O bond angle: 98.36°.

2. The pharmaceutical composition of claim 1, wherein the tetraarsenic hexoxide is prepared by:
   a first step of heating sodium chloride at 100~800° C., followed by cooling;
   a second step of placing arsenic trioxide ($As_2O_3$) on the sodium chloride, followed by heating from 100° C. to 1000° C. in an airtight state and then cooling;
   a third step of separating crystals crystallized in a filter bed collecting sublimated arsenic; and
   a fourth step of repeating the second and third steps four to ten times using the crystals obtained in the third step instead of the arsenic trioxide in the second step, thereby obtaining tetraarsenic hexoxide crystals.

3. The pharmaceutical composition of claim 1, wherein the tetraarsenic hexoxide has a purity of 99.9% or higher.

4. The pharmaceutical composition of claim 1, wherein in the X-ray powder diffraction spectrum of the crystalline polymorph a, obtained by using a light source wavelength of 1.5406 Å within a diffraction angle (2θ) of 10° to 50° at a rate of 1°/min (scan step of 0.02°), peaks are shown at 2θ values of 13.84, 27.88, 32.32, 35.3, 39.84, 42.38, 46.34, 48.6, and 49.34.

5. A pharmaceutical composition containing tetraarsenic hexoxide ($As_4O_6$) as an active ingredient for inhibition of breast cancer metastasis, wherein the tetraarsenic hexoxide includes 99 wt %/o or more of tetraarsenic hexoxide crystalline polymorph a having features (i) to (iii) below:

(i) Cell parameters:
a=b=c=11.0734 Å
α=β=γ=90°
V=1357.82 Å³
(ii) As—O bond length: 1.786 Å
(iii) O—As—O bond angle: 98.36°.

* * * * *